United States Patent
Kholwadwala et al.

(10) Patent No.: US 7,426,873 B1
(45) Date of Patent: Sep. 23, 2008

(54) MICRO ELECTRO-MECHANICAL SYSTEM (MEMS) PRESSURE SENSOR FOR FOOTWEAR

(75) Inventors: Deepesh K. Kholwadwala, Albuquerque, NM (US); Brandon R. Rohrer, Albuquerque, NM (US); Barry L. Spletzer, Albuquerque, NM (US); Paul C. Galambos, Albuquerque, NM (US); Jason W. Wheeler, Albuquerque, NM (US); Clinton G. Hobart, Albuquerque, NM (US); Richard C. Givler, Albuquerque, NM (US)

(73) Assignee: Sandia Corporation, Albuquerque, MN (US)

( * ) Notice: Subject to any disclaimer, the term of this patent is extended or adjusted under 35 U.S.C. 154(b) by 198 days.

(21) Appl. No.: 11/417,755

(22) Filed: May 4, 2006

(51) Int. Cl.
G01N 3/08 (2006.01)
G01B 7/16 (2006.01)

(52) U.S. Cl. .......................... 73/818; 73/777

(58) Field of Classification Search ............ 73/760–856
See application file for complete search history.

(56) References Cited

U.S. PATENT DOCUMENTS

| | | | |
|---|---|---|---|
| 3,643,351 A * | 2/1972 | Eckerlin et al. ............ 36/83 |
| 4,814,661 A | 3/1989 | Ratzlaff et al. |
| 5,373,651 A | 12/1994 | Wood |
| 5,471,405 A | 11/1995 | Marsh |
| 5,929,332 A | 7/1999 | Brown |
| 6,031,463 A | 2/2000 | Bechmann |
| 6,122,846 A | 9/2000 | Gray et al. |
| 6,195,921 B1 | 3/2001 | Truong |
| 6,662,667 B2 * | 12/2003 | Kobayashi et al. ............ 73/849 |
| 6,808,462 B2 | 10/2004 | Snyder et al. |
| 6,865,825 B2 | 3/2005 | Bailey, Sr. et al. |
| 2004/0154190 A1 | 8/2004 | Munster |
| 2005/0172517 A1 | 8/2005 | Bledsoe et al. |
| 2005/0188566 A1 | 9/2005 | Whittlesey et al. |

OTHER PUBLICATIONS

Paradiso, JA, et al., "Design and Implementation of Expressive Footwear", IBM Systems Journal; 2000; vol. 39, No. 3-4, pp. 511-529.
Paradiso, JA, "Footnotes:Personal Reflections on the Development of Instrumented Dance Shoes and their Musical Applications", in Quinz, E., ed., Digital Performance, Anomalie, digital_arts vol. 2, Anomos, Paris, 2002, pp. 1-23.
Paradiso, JA, et al., "Interfacing to the Foot, Apparatus and Applications", Proceedings of the ACM CHI 2000 Conference, pp. 175-176.

(Continued)

*Primary Examiner*—Max Noori
(74) *Attorney, Agent, or Firm*—Koestner Bertani LLP; William R. Conley (57) ABSTRACT

Footwear comprises a sole and a plurality of sealed cavities contained within the sole. The sealed cavities can be incorporated as deformable containers within an elastic medium, comprising the sole. A plurality of micro electro-mechanical system (MEMS) pressure sensors are respectively contained within the sealed cavity plurality, and can be adapted to measure static and dynamic pressure within each of the sealed cavities. The pressure measurements can provide information relating to the contact pressure distribution between the sole of the footwear and the wearer's environment.

13 Claims, 6 Drawing Sheets

OTHER PUBLICATIONS

Morris, Stacy J., et al., "Shoe-Integrated Sensor System for Wireless Gait Analysis and Real-Time Feedback", Proceedings of teh 2$^{nd}$ Joint IEEE EMBS and BMES Conference, Oct. 2002, pp. 2468-2469.

Matt Kelly, "MEMS and Movement Make Beautiful Music Together", http://www.smalltimes.com/print_doc.cfm?doc_id=2826, Jan. 02, 2002, retrieved from the internet Mar. 7, 2006.

Billing, Dan, et al., "In-Shoe Measurement for Biomechanical Monitoring", Proceedings of the Knowledge and Innovation (K&I) Program, Industrial Research Institute, Swinburne, Australia, Jul. 2002, pp. 197-204.

Wheeler, J. et al., "In-Sole MEMS Pressure Sensing for a Lower-Extremity Exoskeleton", presented at BioRob 2006, The First IEEE/RAS-EMBS International Conference on Biomedical Robotics and Biomechatronics, Feb. 20-22, 2006, Pisa, Italy.

* cited by examiner

MICRO ELECTRO-MECHANICAL SYSTEM (MEMS) PRESSURE SENSOR FOR FOOTWEAR

STATEMENT REGARDING FEDERALLY SPONSORED RESEARCH OR DEVELOPMENT

This invention was developed under Contract DE-AC04-94AL85000 between Sandia Corporation and the U.S. Department of Energy. The U.S. Government has certain rights in this invention.

BACKGROUND

A number of in-shoe systems exist for monitoring contact forces and pressures in various environments, for example clinical environments. A common method uses force sensitive resistors positioned around a foot/shoe interface although accuracy and reliability of the resistive sensors is limited. A relatively slow response time of the force sensitive resistor sensors in systems precludes use in real-time control applications. In addition, the sensors are not sufficiently robust or reliable to be used in demanding environments. Load cells can supply multi-axis force data and are more accurate and reliable, however are too large and heavy to allow multi-site data collection, within the limited form factor of a shoe.

In one example of an in-shoe sensor application, a lower-extremity exoskeleton robot can be used to increase a person's payload capacity and endurance. The Berkeley Lower-Extremity Exoskeleton (BLEEX) is an example of such a device. The BLEEX system senses the wearer's intended movements and generates additional force. The system is self-powered, robust and durable. Ground contact pressure information can be supplied to the robot's control system enabling more reliable control in rugged environments. For example, a robot that senses the phase of a wearer's gait can form a more intelligent response. If the robot simply amplifies all sensed forces, events such as hitting a toe on a rock could be worsened by the exoskeleton control system.

SUMMARY

According to an embodiment of sensor-enabled apparel, footwear comprises a sole and a plurality of sealed cavities contained within the sole. The sealed cavities can be incorporated as deformable containers within an elastic medium, comprising the sole. A plurality of micro electro-mechanical system (MEMS) pressure sensors are respectively contained within the sealed cavity plurality, and can be adapted to measure static and dynamic pressure within each of the sealed cavities. The pressure measurements can provide information relating to the contact pressure distribution between the sole of the footwear and the wearer's environment.

BRIEF DESCRIPTION OF THE DRAWINGS

Embodiments of the invention relating to both structure and method of operation can best be understood by referring to the following description and accompanying drawings.

DETAILED DESCRIPTION

An in-sole ground contact pressure sensing system comprises an array of Micro-Electromechanical Systems (MEMS) pressure transducers, disposed in cavities within an elastic medium comprising the sole of a footwear. Aspects of the system include a concept of operation, footwear, and design of pressure transducers, electronics, and packaging. The system enables operation of an accurate and robust method for monitoring contact forces at multiple points on the sole.

Various embodiments of a sensing system enable an accurate and lightweight technique for measuring ground contact pressures in a highly robust manner. The sensing system can be specifically designed to function in harsh environments for a large number of cycles and with good reliability.

Figure 1A:
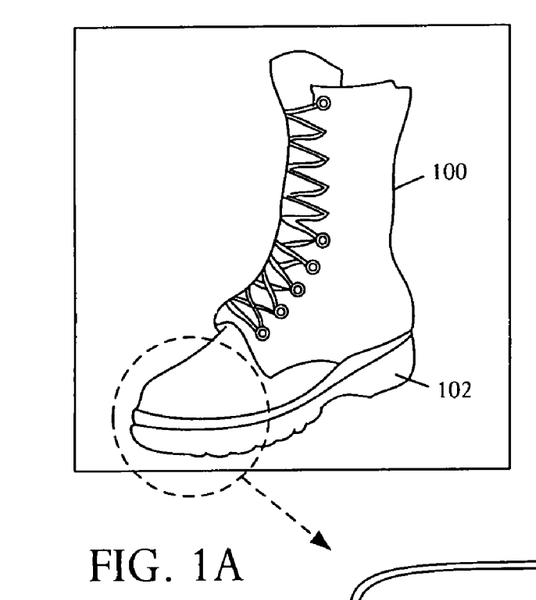
FIGS. 1A, 1B, 1C, and 1D are a set of pictorial diagrams that depict an embodiment of sensor-enabled footwear adapted to monitor contact forces and pressures.

Referring to FIGS. 1A, 1B, 1C, and 1D, a set of pictorial diagrams depict an embodiment of sensor-enabled footwear 100 adapted to monitor contact forces and pressures. FIG. 1A shows a perspective view of the footwear 100, in the illustrative example a boot although any suitable type of footwear can be enabled with the MEMS pressure sensors 106. The footwear 100 comprises a sole 102. Multiple sealed cavities 104 are contained within the sole 102. Multiple micro electro-mechanical system (MEMS) pressure sensors 106 are distributed in the sole 102 and contained within the sealed cavities 104.

Figure 1B:
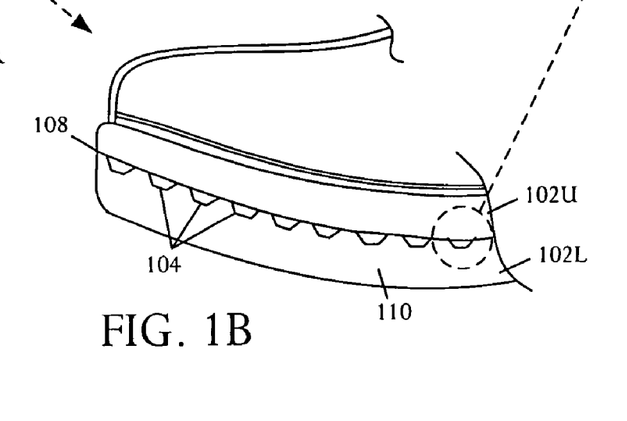

FIG. 1B illustrates a cut-away view of the toe section of the footwear 100. In an example embodiment, the footwear 100 can be implemented as a lower sole 102L and an upper sole 102U and a substrate 108 coupled between the lower sole 102L and the upper sole 102U. An array of the micro electro-mechanical system (MEMS) pressure sensors 106 contained in elastic media 110 are shown coupled to the substrate 108 and encapsulated within the cavities 104 in the elastic media 110. Examples of elastic media 110 can include leather, rubber materials, synthetic elastics, silicon rubber, ethylene vinyl acetate (EVA) and other flexible materials including materials commonly used in the fabrication of soles for footwear.

In some embodiments, the MEMS pressure sensors 106 are encapsulated within sealed cavities 104 formed within an elastic medium, and where required by an application, the MEMs pressure sensors 106 could be hermetically sealed within the cavities 104 (e.g. enclosed in hermetic packaging). The cavities are defined to be sealed with respect to leakage of air or other working fluids, when any leakage into or out of the cavity is low enough to permit the MEMS pressure sensor to obtain an accurate reading of pressure within the cavity, i.e. before leakage would degrade the accuracy of the measured pressure value more than required for a given application. The array of MEMS pressure sensors 106 is adapted to measure pressures within the cavities 104, formed in the elastic media 110. FIG. 1B illustrates the cavities 104 distributed throughout the sole 102 of the boot 100, allowing measurement of the pressure distribution across the sole 102, and therefore determination of the distribution of contact forces between the sole and the wearer's environment.

In an example implementation, silicon micro-machined pressure sensors 106 can be integrated into an array of airtight sealed cavities 104 within the sole 102 of a boot. Pressure on the sole 102 causes the cavities 104, formed within an elastic media 110, to be compressed. The air pressure within each cavity 104 increases with local compression of the sole 102. A MEMS pressure sensor 106 can sense the absolute pressure within each cavity 104. A coordinated output signal from the pressure sensors 106 produces a pressure profile across the entire sole surface.

Figure 1C:
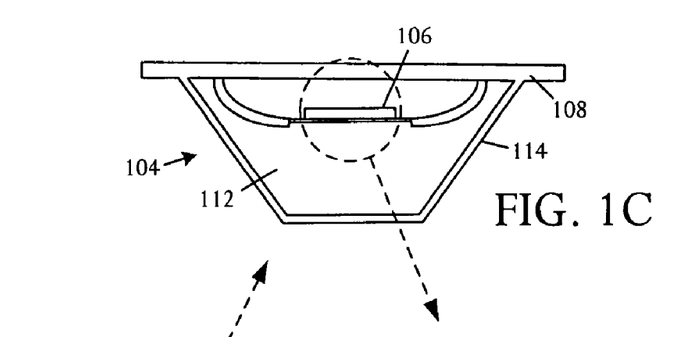

FIG. 1C shows a cut-away view of a cavity 104 containing a MEMS pressure sensor 106. An illustrative sensor element 112 comprises a deformable container 114 comprising an elastic media, configured to encapsulate an airtight sealed cavity 104 and a micro electro-mechanical system (MEMS) pressure sensor 106. The MEMS pressure sensor 106 is sealed into the cavity 104 within the container 114 and is adapted to measure pressure (or changes in pressure) within the cavity 104.

Figure 1D:
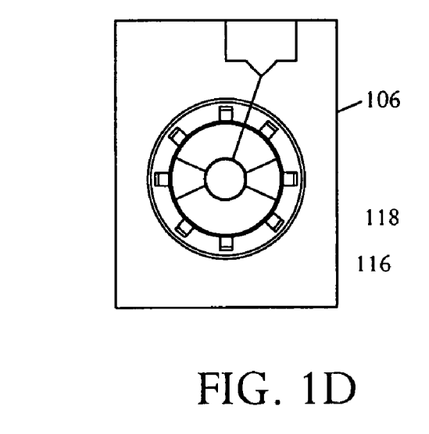

FIG. 1D illustrates an example of a MEMS pressure sensor 106 that can be encapsulated within the container 112. In some embodiments, the MEMS pressure sensor 106 can be a surface micro-machined pressure transducer constructed from a deformable membrane 116 with integrated piezoresistive traces 118 formed on the membrane 116. Piezoresistive traces can comprise any material that experiences a change in resistivity, conversely conductivity, under the influence of an applied load (e.g. stress or strain).

Figure 2A:
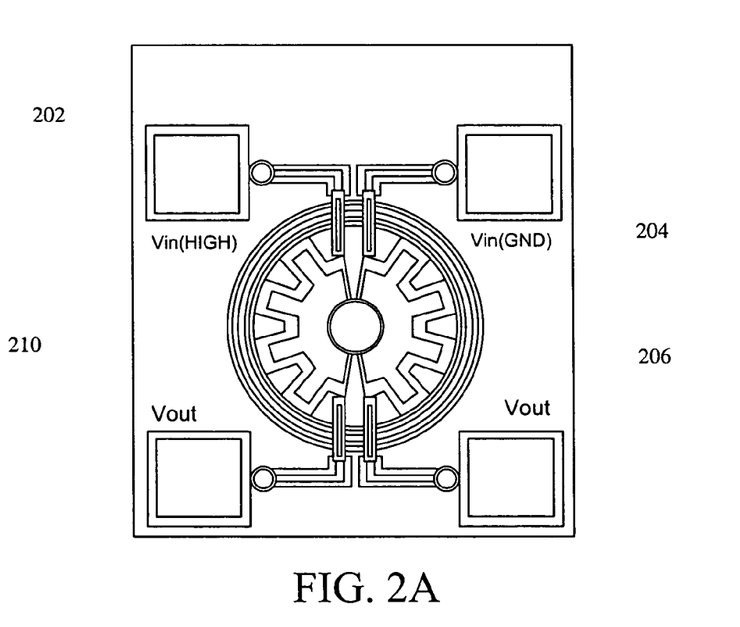
FIGS. 2A and 2B are schematic pictorial diagrams respectively showing a top view of an optical microscope image and a side view of an embodiment of a micro electro-mechanical systems (MEMS) pressure sensor that is suitable for usage in elastic media preparations.
Figure 2B:
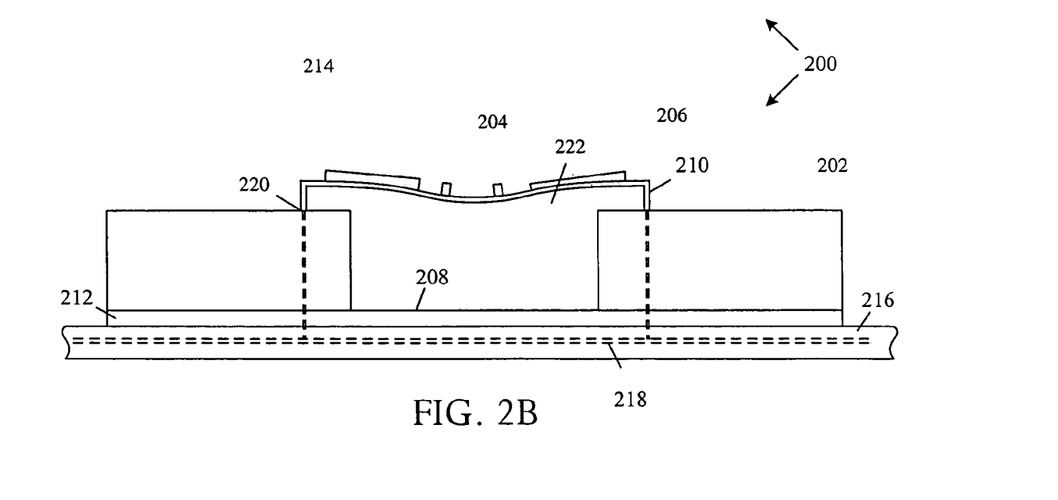

Referring to FIGS. 2A and 2B, schematic pictorial diagrams respectively show a top view of an optical microscope image and a side view of an exemplary micro electro-mechanical systems (MEMS) pressure sensor 200 that is suitable for usage in elastic media preparations, for example footwear. A MEMS pressure sensor 200 may be fabricated in a silicon die 202. The sensor 200 may comprise a flexible drum-head diaphragm 210 and piezo-resistive traces 204 and 206 disposed onto the flexible drum-head diaphragm 210. In some implementations, the traces may be patterned in a half- or full-Wheatstone Bridge configuration whereby a change in resistance correlates to a resulting analog signal. The illustrative sensor 200 further comprises a reference cavity 222 abutting and separated by the diaphragm 210 from the sensed cavity 214 e.g. the cavity housing the sensor 200. The reference cavity 222 is typically maintained at a constant pressure. The sensed cavity 214 corresponds to the cavity 104 shown in FIGS. 1B and 1C.

The principle of operation of various MEMS transducer designs is generally similar. The flexible drum-head diaphragm 210 separates the sensed cavity 214 from the reference cavity 222 which may be machined into the silicon die 202. Pressure in the reference cavity 222 is maintained constant. As pressure in the sensed cavity 214 increases, the diaphragm 210 flexes (i.e. is deflected) changing the effective resistance of the piezo-resistive traces 204 and 206 etched onto the flexible diaphragm 210. The traces 204 and 206 are formed into a pattern suitable for sensing, for example a half- or full-Wheatstone Bridge configuration so that a change in resistance can be correlated to a resulting analog voltage signal. In various embodiments, the size and shape of the diaphragm 210 and the trace configurations may have any suitable form.

The silicon die 202 comprising the MEMS pressure sensor 200 can be bonded to a stiffener 212 which is in turn bonded to a flexible printed wiring board 216. The flexible printed wiring board 216 contains conductors 218 for interconnecting power and signal connections to the sensor 200. The stiffener 212 forms a locally rigid mounting surface 208, that can facilitate assembly of pressure sensor 200 to a flexible printed wiring board 216. The flexible printed wiring board 216 can be constructed of polyimide or other materials typically used in the manufacture of flexible printed wiring boards. Stiffeners can comprise metallic, ceramic, glass-ceramic or polymeric materials, less flexible that the flexible printed wiring board to which the stiffener is bonded. In some embodiments a stiffener can comprise an additional localized layer of polyimide material, bonded to a polyimide, flexible printed wiring board (i.e. a flexible circuit board). Bonding the die 202 to the stiffener 212 and likewise bonding the stiffener 212 to the printed wiring board 216 can be accomplished by conventional means including the use of adhesives, adhesive tapes, and solders. Interconnection of conductors 218 in the flexible printed wiring board 216 to the traces 204, 206 of the MEMS die 202 can be made by backside connections 220 incorporated into the die 202 (as shown) or could alternatively be made by means including wire bonds, flip chip attach, and soldering. In this example, the MEMS pressure sensor 200 is shown as a bare silicon die 202, eventually attached to a flexible printed wiring board 216. Alternatively, the MEMS pressure sensor 200 could be contained within an package such as a dual inline package (DIP) ball grid array package (BGA) pin grin array package (PGA) surface mount package (SMT package) through-hole package or the like. As illustrated, the reference cavity 222 can be machined as a through-hole in the silicon die 202 or alternatively can comprise a depression or cavity formed within the silicon die.

In an implementation such as the footwear 100 depicted in FIGS. 1A through 1D, the flexible printed wiring board substrate 216 can be used as the substrate 108 interposed between the upper sole 102U and the lower sole 102L. In embodiments of the invention, the cavities can enclose volumes of trapped air or other gases as may be introduced into a cavity during the manufacturing process. In other embodiments of the invention, it can be desirable to fill the cavities with a working fluid, such as water, oil or inert (e.g. fluorinated) fluids.

Referring to FIGS. 3A, 3B, 3C, and 3D, multiple pictorial diagrams illustrate an embodiment of a sensor-enabled exoskeletal boot 300 including an in-sole ground contact force sensing system using MEMS pressure transducers 306 arrayed in sealed cavities 304. A micro electro-mechanical system (MEMS) transducer array 320 can be mounted to a flexible printed wiring board 308 to sense a pressure profile within the sole 302 of an exoskeletal boot 300. The MEMS transducer array 320 comprises multiple MEMS devices distributed in independent airtight cavities 304 that function as pressure sensors 306 and measure a load distribution profile between a contact surface, e.g. the ground, and the boot 300. The individual MEMS sensors 306 can be used to determine local loads by measuring changes in pressure within the sealed, deformable cavity 304. The MEMS pressure sensors 306 can be arrayed throughout the boot sole 302 and configured to measure both dynamic and static pressures.

The MEMS transducer array 320 can be constructed as surface micro-machined pressure transducers 306 including piezo-resistive elements, for example doped polysilicon traces 318, deposited over an insulating membrane 316 that deflects under a pressure differential. In a particular example, the membrane 316 can be constructed from a silicon nitride layer. Strain in the traces 318 that results from the deflection changes the traces resistance. The resistance change can be balanced with a Wheatstone Bridge circuit to generate a voltage that is proportional to pressure. The Wheatstone Bridge circuit can be fabricated in the same substrate, i.e. a silicon die, as the pressure sensor itself.

The array 320 of MEMS pressure sensors 306 in the exoskeletal boot 300 sense the pressure profile within the sole 302. The exoskeletal boot 300 can further comprise a communication interface 322 coupled to the MEMS pressure sensors 306 in the array 320 that supplies ground contact pressure information to a robotic control system 324. For example, in some embodiments, power 328 and signal wires 330 are arranged to extend through the sole 302 and couple to the MEMS pressure sensor array 320. Data acquisition and control electronics 334 placed on a robot external to the sole 302 couple to the MEMS pressure sensor array 320 via the power 328 and signal wires 330.

In an example application, a control system for an exoskeleton boot (exoboot) uses ground contact pressure information to operate safely and effectively. Commercially available in-sole sensors do not have sufficient bandwidth, accuracy and reliability for such a system. The in-sole ground contact sensor system disclosed herein uses MEMS pressure transducers 306 placed in an array 320 of sealed cavities 304, enabling a system configured to execute a robust method of monitoring ground contact pressures.

The sensor-enabled exoskeletal boot 300 can be configured as a boot-ground pressure profiler that monitors balance and senses terrain, enabling an exoskeletal device to effectively control stance and gait. The illustrative MEMS pressure sensor array enables operation that avoids difficulties of conventional pressure sensor arrays that are either too bulky or have excessive draft. The illustrative MEMS-based pressure sensor enables a highly unobtrusive, high-resolution array with good constant-pressure measurement performance.

Figure 3A:
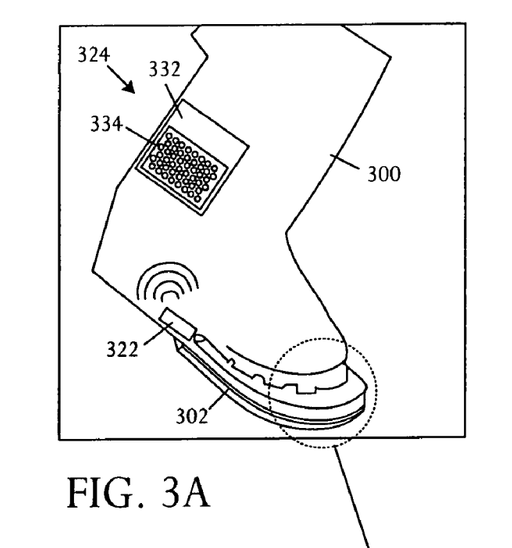
FIGS. 3A, 3B, 3C, and 3D are multiple pictorial diagrams illustrating an embodiment of a sensor-enabled exoskeletal boot including an in-sole ground contact force sensing system using MEMS pressure transducers arrayed in sealed cavities.
Figure 3B:
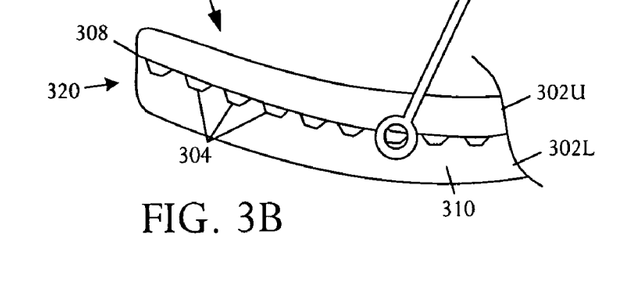

FIG. 3A is a perspective pictorial view showing the exoskeletal boot 300. FIG. 3B illustrates a two-piece sole 302 formed within or under the boot 300. The sole 302 contains the array 320 of sealed cavities 304. The sole 302 can be constructed, for example, of two rubber or other material parts, an upper sole 302U and a lower sole 302L, that enable sensors 306 and electronics to be placed inside the cavities 304.

Figure 3C:
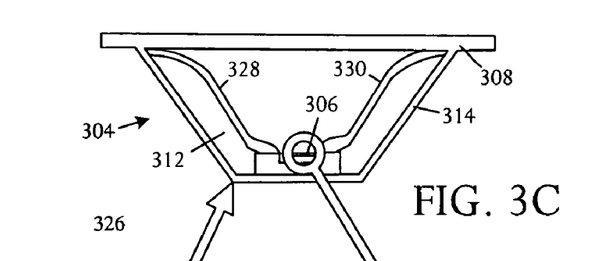

FIG. 3C shows an embodiment of an individual pressure sensor element 312 of a MEMS array 320. The sensor element comprises a deformable container 314 comprising an elastic media, encapsulating an airtight sealed cavity 304. The deformable container 314 is configured to increase air pressure internal to the cavity 304 in response to local compression of the container 314. One or more micro electro-mechanical system (MEMS) pressure sensors 306 are sealed into the cavity 304 within the container 314 and adapted to sense dynamic and static pressures within the cavity.

Power wires 328 and signal wires 330 extend through the sole 302 and couple to the individual sensors 306 of the MEMS pressure sensor. The wires can connect the sensors 306 to an electronics module 332, for example that can be attached to the exoskeletal boot 300. The electronics module 332 is communicatively coupled to the MEMS pressure sensors 306 in the array 320 and is adapted to measure a load distribution profile between a surface and the boot 300.

In a particular implementation, signal traces can be routed through the insole region and extend to the electronics module 332 located, for example, on an external surface of the boot 300. On-board processing and signal acquisition logic can be included to interpret raw acquired sensor data and communicate the results to a supervision system, for example via a wireless communication link. Signal handling and communication electronics can be contained within a low profile electronics enclosure. Both the enclosure and the signal wires can be protected from moisture, abrasion, and shock that are likely to be experienced during usage.

In some embodiments, the pressure sensor element 312 can also include electronics, such as a data acquisition and signal processing element 326 coupled to the micro electro-mechanical system (MEMS) pressure sensor 306 in combination. The combined sensor 306 and data acquisition and signal processing element 326 can be sealed into the cavity 304, for example, in an application where the MEMS pressure sensor and data acquisition and signal processing element are fabricated on the same silicon die.

Figure 3D:
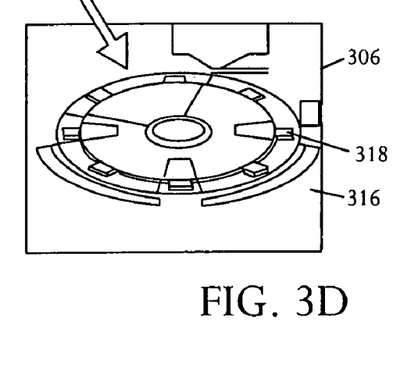

FIG. 3D is an optical microscope image illustrating a deformable membrane pressure sensor 306. The MEMS pressure sensor 306 in the illustrative embodiment is configured as a silicon surface micro-machined pressure transducer 306 comprising a deformable membrane 316 and a plurality of integrated piezoresistive traces 318 disposed and patterned onto the deformable membrane 316.

In some embodiments, the MEMS pressure sensors 306 in the pressure sensor array 320 can be configured as unpackaged silicon micro-machined pressure sensor components integrated into airtight sealed cavities and adapted to measure dynamic pressure and static pressure.

Small, lightweight MEMS pressure transducers can be used to enable sensing at high spatial resolution. Unpackaged integrated circuits can be implemented or signal processing electronics can be located external of the sealed cavities to enable creation of an array of smaller, more closely placed cavities.

The sensor-enabled footwear 300 is typically operated by sensing contact pressure from the array 320 of micro electro-mechanical system (MEMS) pressure sensors 306 which are encapsulated and sealed in the cavities 304 distributed in the footwear sole 302. As the sole 302 comes into contact with the ground, the cavities 304 are compressed, causing an internal increase in air pressure. The pressure is measured by the pressure sensors 306. Power 328 and signal 330 wires are placed throughout the sole 302. Data acquisition and control electronics 334 can be placed on the robot, external to the sole 302. The data acquisition and control electronics 334 interprets the contact pressure signals and communicates the contact pressure signal interpretations to a supervisor system. The supervisor system generates a dynamic pressure profile and a static pressure profile from the communicated contact pressure signal interpretations. The supervisor system can monitor the balance of the robotic (e.g. exoskeletal) structure from the dynamic pressure profile and the static pressure profile.

Referring again to FIGS. 2A and 2B, microscopic perspective and top views depict an embodiment of a surface micro-machined pressure sensor 200 comprising a deformable membrane 210 and integrated piezoresistive traces 204 and 206. In an example embodiment, the MEMS pressure transducer 200 is constructed using a SUMMiT™ process and a SwIFT™ process. The SUMMiT™ process specifies a MEMS structure comprising five layers of polysilicon enabling construction of complex MEMS structures. The SwIFT™ process includes the SUMMiT™ process supplemented by additional transparent and insulating silicon nitride layers. The pressure sensor can use piezoresistive elements, for example doped polysilicon traces, deposited over an insulating membrane, such as a silicon nitride membrane, that deflects under a pressure differential. Resulting strain in the traces 204, 206 changes trace resistance, a change that can be balanced with a Wheatstone Bridge circuit to generate a voltage that is proportional to pressure. In fault tolerant designs, multiple transducers can be included in a redundant formulation on the same silicon die 202, with no additional packaging. An example of a surface micromachined pressure sensor of the type illustrated in FIG. 2A, can have a die size ranging from on the order of 1 mm$^2$ to 1 cm$^2$.

The microscope image of a full-bridge design shown in FIG. 2A and a drawing depicted in FIG. 2B describe the transducer principle of operation. In full-bridge designs, two sets of traces 206 experience tension and two sets of traces 204 experience compression when the membrane 210 is flexed. In the half-bridge designs, two of the traces are off the membrane, typically resulting in a less-sensitive device.

Figure 4:
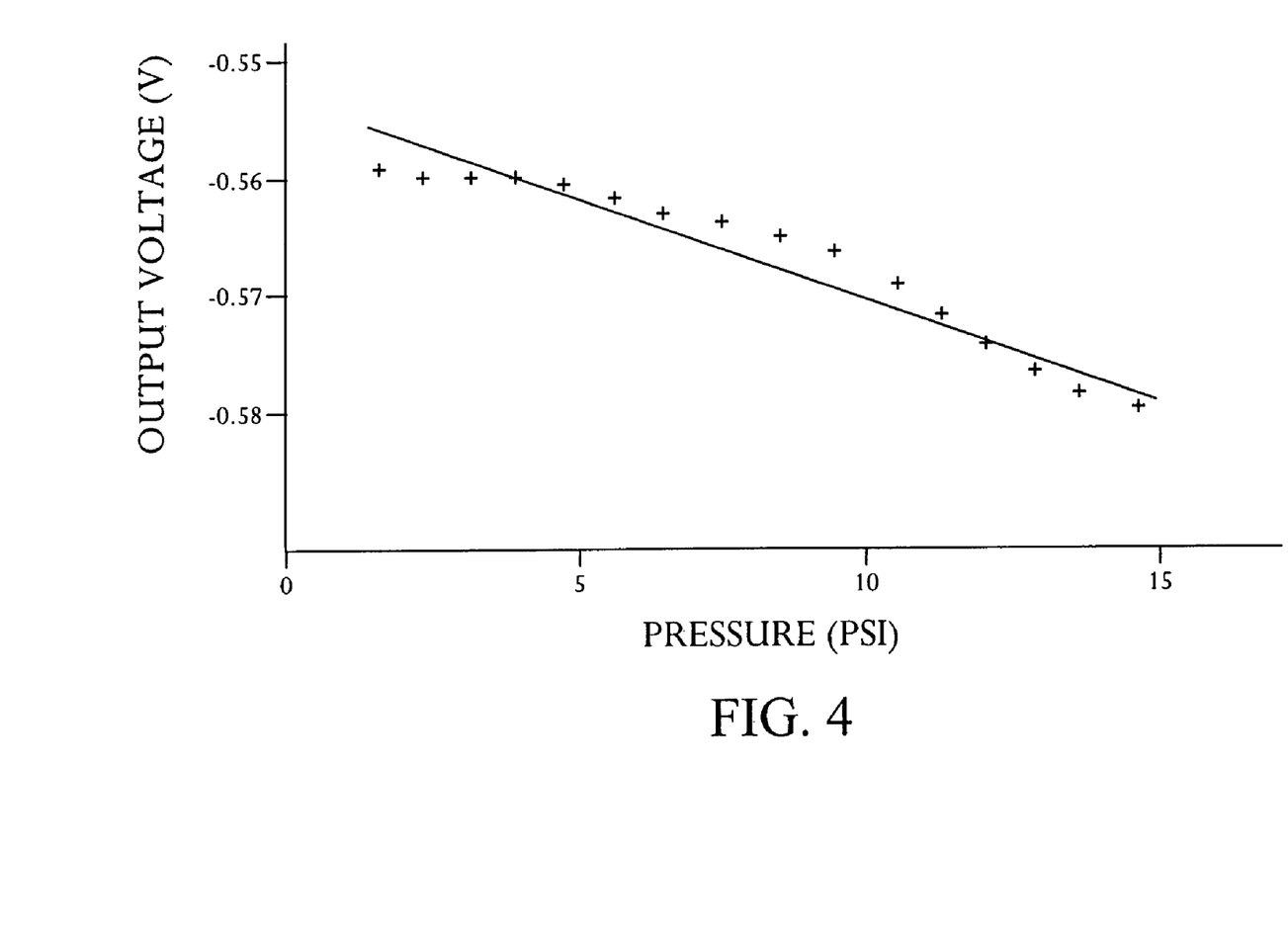
FIG. 4 is a graph showing output voltage versus pressure data for the device type shown in FIGS. 2A and 2B.

FIG. 4 is a graph that shows the response of an actual tested device as output voltage versus pressure difference data for the device type shown in FIGS. 2A and 2B. The axis labeled "pressure" in the graph represents the differential pressure between the sensed cavity (i.e 214 in FIG. 2B) and the reference cavity (i.e. 222 in FIG. 2B). In applications where the reference cavity is maintained at zero pressure (i.e. a vacuum) the pressure measured would be the "absolute" pressure of the sensed cavity. The graph also shows a linear fit to the data. Although the data shown in FIG. 4 is approximately linear with root mean square deviation from a linear fit at 4.3% of the range, a quadratic model fits the data much better, having a root mean square deviation from a quadratic fit of 1.1% of the range and the fit can be simply implemented in a post-processor or other control logic, for example implemented in a control module. Repeatability of the measurements is highly suitable with subsequent measurements showing a standard deviation of 0.2 mV. The measurements show good stability as well, typically changing by 0.1 mV or less within the first minute after the pressure is changed. Various transducer designs have shown good reliability and robustness with measurement repeatability maintained after thousands of pressure cycles.

The data shows a significant non-zero offset of –0.558 V which is attributed to residual stress in the membrane 210 that can limit measurement resolution. Such residual stress can be reduced through usage of on-die trim resistors that enable a much lower offset and higher measurement resolution. Other operating characteristics can be attained through optimization for measurement sensitivity, ruggedness of the membrane, and ease of packaging.

The illustrative sensor-enabled footwear can be designed and produced by forming an array of cavities within a footwear sole and integrating a plurality of micro electro-mechanical system (MEMS) pressure sensors into the cavity array. The pressure sensor array is encapsulated within airtight sealed cavities in the cavity array in a configuration that enables pressure measurement.

Figure 5:
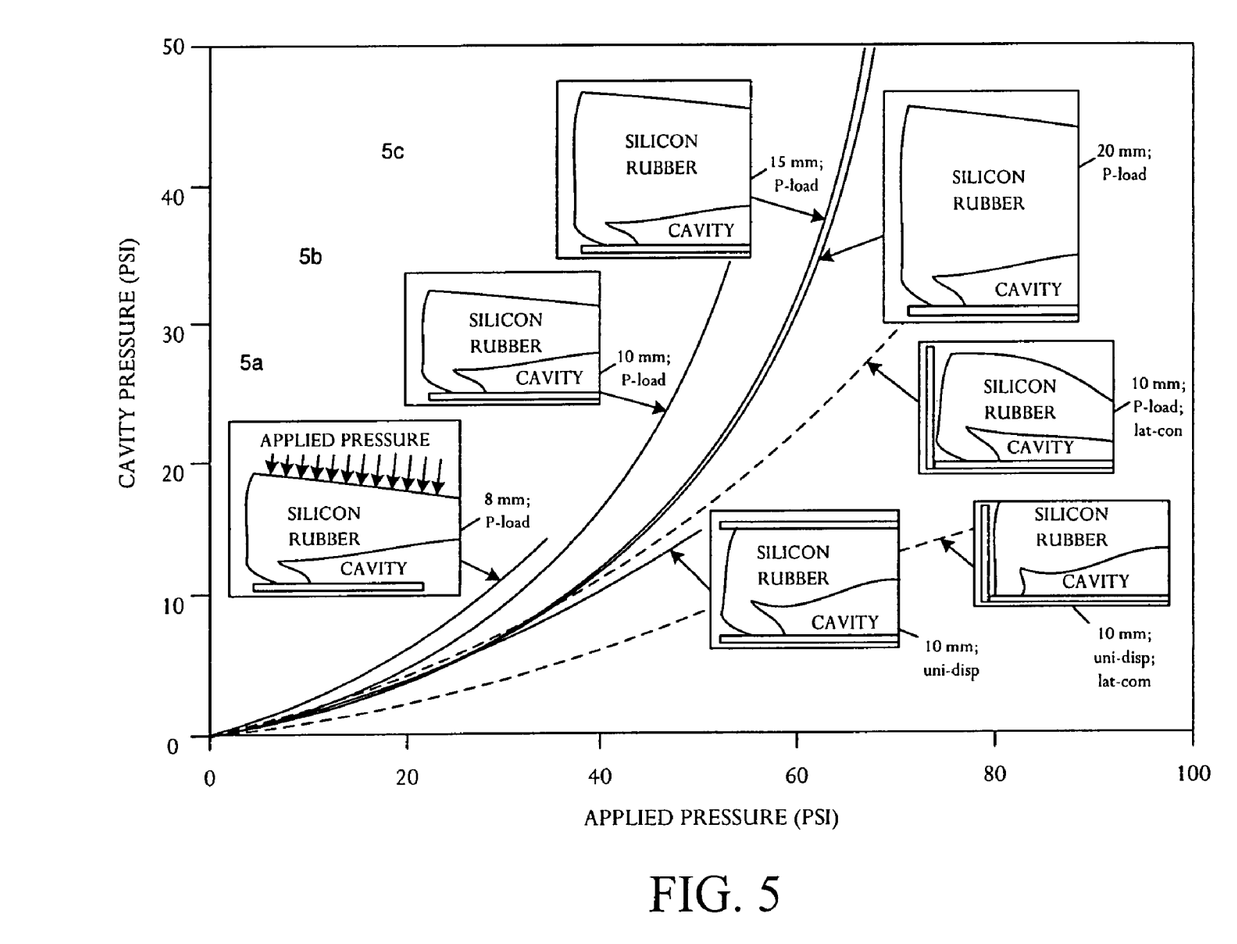
FIG. 5 is a graph depicting a finite element analysis of various sole thickness and boundary constraints for pressure cavities.

The cavity containing the transducer is designed for good sensitivity while ensuring that the MEMS pressure sensor and any associated electronics are not crushed as the cavity is compressed. Finite element analyses can be performed to assess the pressure and displacement characteristics for multiple various designs and/or configurations. The results of several such analyses are graphically summarized in FIG. 5 which depicts a finite element analysis of various sole thickness and boundary constraints for cavities. For example, the series 5a, 5b and 5c illustrate the effect of increasing the thickness of the elastic media (e.g. silicone rubber) over an example cavity, on the pressure measured within the cavity as a function of applied pressure. The cavities are illustrated in the deformed state, under the action of the applied pressure. Cavity dimensions can be selected based on the expected geometry of the sensors and electronics and appropriate air pocket size, while sole thickness and boundary constraints are varied. Cavity size and shape can be modified to accommodate the variations in the finite element analyses. Various elastic materials, for example rubber-like materials, can be compared using similar analyses.

Figure 6:
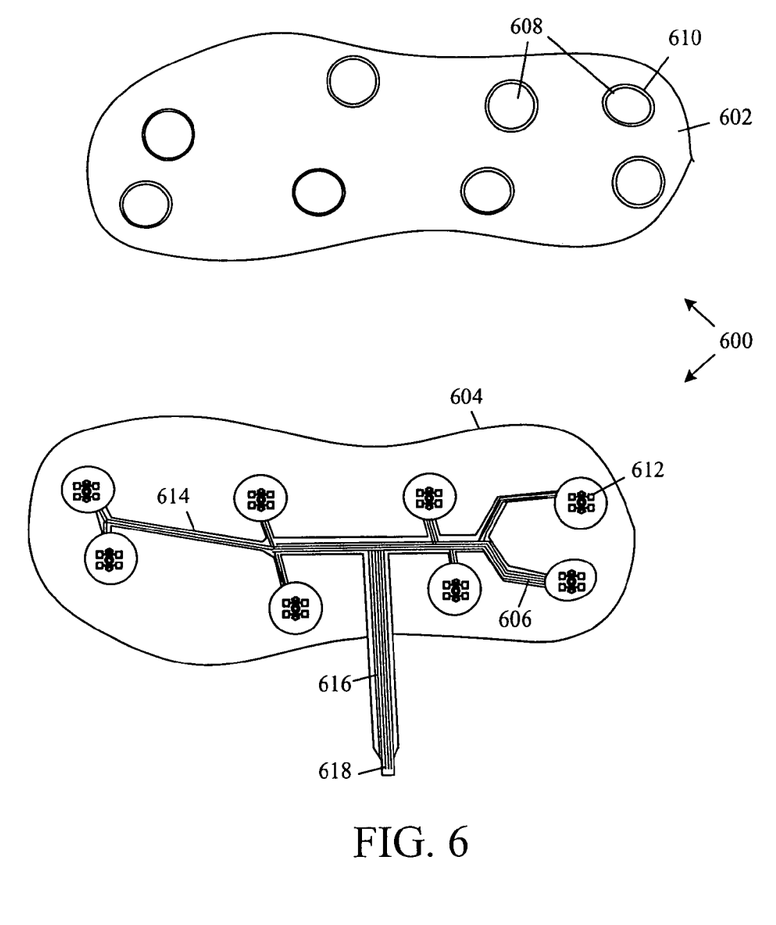
FIG. 6 is a pictorial overhead view illustrating lower and upper portions of an embodiment of a sensor-enabled sole.

Referring to FIG. 6, a pictorial overhead view illustrates lower 602 and upper 604 portions of an embodiment of a sole 600 including a flexible printed wiring board 606 placed in the upper sole 604. The sole 600 is constructed with cavity dimensions determined by the finite element analysis. Selected dimensions can correspond to the cavity configuration that is most sensitive to external loads while not collapsing enough to harm the components within a cavity, under a maximum expected pressure, for example 70 psi. The lower sole 602 contains the cavities 608, while the upper portion 604 contains areas for flexible circuit board routing. The illustrative prototype contains eight cavities 608 placed at locations determined to suitably indicate the wearer's gait phase. Rings 610 surrounding the cavities 608 can be added to improve sealing while facilitating the mutual isolation of multiple isolated unpackaged silicon micro-machined pressure sensor components 612 within individual air pockets integrated into the footwear sole. Air pressure sensors 612 are configured and encapsulated to measure contact pressures in an elastic media in the sole 600. The array of air pressure sensors can be surface mounted in the cavities 608.

The sensors 612 and electronics can be assembled to the flexible printed wiring board as described above, and the two sole pieces 602, 604 sealed together with an adhesive, completing the seal around each cavity 608 and forming a package that is waterproof and robust to rugged terrain. A suitable adhesive can be selected that enables usage over-thousands of cycles in the sole 600 without delamination.

The sensor 612 can be formed by obtaining a flexible drum-head diaphragm and patterning piezo-resistive traces in a half- or full-Wheatstone Bridge configuration whereby a change in resistance correlates to a resulting analog signal. The patterned piezo-resistive traces can be formed by etching polysilicon films deposited onto a flexible drum-head diaphragm, that can comprise a silicon nitride membrane. A reference cavity can be machined into the sensor that abuts, and is separated from the sensed cavity by the diaphragm. The reference cavity is generally maintained at a constant pressure during usage.

A flexible printed wiring board 614 can comprise conductors 616 to supply power and signal connections to the sensors 612 and front-end electronics in the flexible sole 600. Individual sensors 612 within the pressure sensor array can be mounted to the flexible printed wiring board 614 with power and signal connections routed from the sensors through the footwear insole region to an electronics module coupled to the footwear. Routing of the conductors 616 on the flexible printed wiring board is configured to ensure that the conductors are not strained excessively as the sole 600 flexes. Excessive strain can lead to fatigue failure. For an illustrative system, a single-layer flexible printed wiring board 614 can be designed so that all electrical traces are located on a neutral axis of the assembled sole 600. In a specific illustrative embodiment, the flexible printed wiring board can comprise 1 oz. copper traces laminated between 0.003" thick polyimide dielectric layers. A stiffener can be applied to the flexible circuit board to form a locally rigid mounting surface, for the sensors 612. Plastic stiffeners can be placed in areas where the sensors and electronics are mounted to promote stability, and facilitate assembly. Although any suitable connector can be used, the board 614 can terminate with a zero-insertion-force (ZIF) connection 618 that interfaces with a data acquisition board. The flexible printed wiring board 600 can be constructed to last for millions of cycles.

Data acquisition and signal processing electronics elements can be contained within the cavities in combination with or as part of the MEMS pressure sensors (i.e. on the same silicon die) thereby encapsulating electronics and sensors into the airtight sealed cavities. The MEMS pressure sensor can be constructed as a half or full-bridge Wheatstone bridge, strain gauge circuit, enabling the sensor pressure to be expressed as a small analog differential voltage. The data acquisition circuit is generally constructed with a capability to condition and sample several small differential voltages, from several sensors, and send the pressure data to the exoskeleton controller. Data acquisition circuit functionality is configured that any delays in gathering and delivering data to the controller are sufficiently small to enable a desired level of control. For example, the data acquisition circuitry is selected to sample data at rates that satisfy the control sampling criteria, for the given application.

For an exemplary 8-sensor application, the data acquisition can be supplied using a simple front-end circuit to interface with each MEMS device and an 8-bit processor to collect the data using eight analog-to-digital converters. The front-end circuit amplifies the differential voltage from the MEMS pressure sensor and shifts the voltage signal upward for centering at half the supply voltage of the processor. The processor can sample each of the eight pressure signals with 10-bits of resolution and subsequently send the combined data packet using the processor's universal asynchronous receiver-transmitter (UART). During continuous sampling and sending of data at 115 kbaud, a system can sample eight sensors and send data over 300 packets per second, implying a maximum delay of less than 3.3 milliseconds, a sufficiently small delay for control purposes.

In contrast to capacitive and piezoelectric pressure sensor arrays, the described MEMS pressure sensor array, encapsulated within the sole enables generation of both dynamic and stable, i.e. static, pressure profiles. Integrated sensors and electronics contained within the sole and/or treads of a boot, enable a sensor system to be created within the size constraints of footwear, without increasing sole thickness or modifying existing boot tread. The sole enables construction of footwear that does not introduce new motion constraints. Sensor-enabled footwear can be fabricated with any tread pattern.

Sensor and electronics components constructed from micro electro-mechanical system (MEMS) devices enable improvements in many characteristics. MEMS are commonly very small and lightweight, desirable properties in many applications. MEMS low inertia enables an extremely high bandwidth and sustainable functionality in the presence of large accelerations, shocks, and high vibration environments. MEMS can be fabricated on a silicon die, simplifying integration with electrical circuits which can be co-located with the MEMS on the same die, while minimizing energy consumption. In addition, economies of scale drive the price of each component to desirable low levels when devices are manufactured in large quantities, as is the case for batch fabrication of MEMS devices.

MEMS devices typically have high resistance to wear and fatigue. Furthermore, due to mutual independence among individual sensors, failure of one avoids susceptibility to a catastrophic system failure. A system can be implemented with a large number of independent sensors to form a highly redundant system that degrades minimally and gracefully with an accumulation of failures, in a manner reminiscent of biological sensor arrays in the skin and eyes.

Some embodiments can implement MEMS devices as bare, unpackaged silicon dice rather than pre-packaged and/or commercially-available MEMS pressure transducers. Usage of silicon dice reduces overall sensor volume, in some implementations by an order of magnitude or more, enabling the sensors to fit within the footwear sole without appreciably changing the dimensions of the footwear. MEMS bare dice mounted in an array on a flexible printed wiring board enables extremely low-profile packaging. Packaging and isolation of sensors within individual cavities integrated into the boot sole facilitates fabrication, operation, and functionality of MEMS devices, reducing susceptibility to damage from contact and contamination of, the small-size and therefore potentially delicate MEMS devices.

Embodiments of the MEMS system that implement a flexible printed wiring board (for example, flexible printed wiring boards manufactured and marketed by All Flex, Inc. of Northfield, Minn.) enable signal and power routing at a density suitable for a continuously-bending sole. Such flexible circuit boards can enable fatigue lifetimes of one million bending cycles or more. Some embodiments can comprise a flexible circuit board with localized polyimide stiffeners at individual transducer locations. The flexible circuit board and/or stiffeners facilitate assembly and maintenance of pressurized, isolated pockets with small separation space, and routing of multiple conductors (i.e. power and signal lines) per cavity. Accordingly, the flexible circuit board and/or stiffeners assist dense population of the sole with MEMS sensors.

The MEMS sensor array can be implemented to accommodate a wide variety of technical specifications. One example implementation can specify spatial resolution of the sensor array at about 1 cm$^2$, a range of 50 pounds per square inch (psi), resolution of about 1% of full scale, hysteresis of less than 5%, drift of less than 5%, overload protection of about 500%, and cycles to failure can be specified. An example communication specification designates a Firewire external communication bus, a suitable communication protocol, and sampling rate of about 500 Hertz.

Pressure spikes beyond maximum range can be acknowledged, and overload protection designed into the sensors. A Firewire output connection can be made accessible on the exterior surface of the boot, e.g. medially, the most protected position on the boot. An external power source from the exoskeleton can be used to supply power and be transformed within the boot. A measuring frequency of 500 Hz or faster can be suitable, depending on selected power source specification. Electronics, wiring, and system hardware can be confined within the boot. During operation, reliability can be defined according to a selected operation of non-stop motion.

While the present disclosure describes various embodiments, these embodiments are to be understood as illustrative and do not limit the claim scope. Many variations, modifications, additions and improvements of the described embodiments are possible. For example, those having ordinary skill in the art will readily implement the steps necessary to provide the structures and methods disclosed herein, and will understand that the process parameters, materials, and dimensions are given by way of example only. The parameters, materials, and dimensions can be varied to achieve the desired structure as well as modifications, which are within the scope of the claims. Variations and modifications of the embodiments disclosed herein can also be made while remaining within the scope of the following claims. For example, the MEMS sensors and transducers are exemplified by particular structures with specific sizes and compositions. Any suitable structures, sizes, and materials can be used as appropriate for a particular application. Furthermore, the MEMS sensors, cavities in elastic media, and array formulations are described in the application of footwear. In other applications, the encapsulated sensors can be implemented in any application of sensors appropriate for usage in an elastic media.

What is claimed is:

1. Footwear comprising:
   a sole; and
   a plurality of sealed cavities contained within the sole; and,
   a plurality of micro electro-mechanical system (MEMS) pressure sensors respectively contained within the sealed cavity plurality.

2. The footwear according to claim 1 further comprising:
   a lower sole and an upper sole, at least one of the lower sole and the upper sole comprising an elastic media, the sealed cavity plurality disposed within the elastic media;
   a flexible printed wiring board coupled between the lower sole and the upper sole; and,
   the plurality of micro electro-mechanical system (MEMS) pressure sensors coupled to the flexible printed wiring board and encapsulated within the cavities in the elastic media, the array of MEMS pressure sensors adapted to measure pressures within the plurality of cavities.

3. The footwear according to claim 2 further comprising:
   a plurality of sensor elements, each sensor element comprising:
   a deformable container coupled to the flexible printed wiring board and configured to encapsulate a sealed cavity; and,
   a micro electro-mechanical system (MEMS) pressure sensor sealed into the cavity within the container and adapted to measure pressure within the cavity.

4. The footwear according to claim 1 further comprising:
   an electronics module communicatively coupled to the MEMS pressure sensor plurality and adapted to measure a load distribution profile between a surface and the footwear.

5. The footwear according to claim 1 further comprising:
   the MEMS pressure sensors in the pressure sensor plurality configured as unpackaged silicon micro-machined pressure sensor components integrated into the sealed cavity plurality and adapted to measure pressure within the plurality of cavities.

6. The footwear according to claim 1 further comprising:
   the MEMS pressure sensors in the pressure sensor plurality configured as silicon surface micro-machined pressure transducers comprising a deformable membrane and a plurality of integrated piezoresistive traces disposed on the deformable membrane.

7. The footwear according to claim 3 further comprising:
   a data acquisition and signal processing element coupled to each micro electro-mechanical system (MEMS) pressure sensor in combination, the combination sealed into the cavity.

8. The footwear according to claim 1 further comprising:
   power and signal conductors extending through the sole and configured to couple individual MEMS pressure sensors of the MEMS pressure sensor plurality, to an electronics module.

9. The footwear according to claim 1 further comprising:
   an exoskeletal boot including the sole, the MEMS pressure sensor plurality adapted to sense a pressure profile within the sole; and,
   a communication interface coupled to the MEMS pressure array adapted to supply ground contact pressure information to a robotic control system.

10. The footwear according to claim 9 further comprising:
    a data acquisition and control electronics coupled to the communication interface.

11. A method for operating micro electro-mechanical system (MEMS) pressure sensor-enabled footwear comprising:
    sensing pressures from an array of micro electro-mechanical system (MEMS) pressure sensors encapsulated and sealed in cavities distributed in a footwear sole;
    interpreting the pressures provided as signals from the array of MEMS pressure sensors;
    communicating the pressure signal interpretations to a supervisory system; and,
    generating a dynamic pressure profile and a static pressure profile from the communicated pressure signal interpretations.

12. The method according to claim 11 further comprising:
    monitoring balance from the dynamic pressure profile and the static pressure profile.

13. The method according to claim 11 further comprising:
    sensing pressures from an array of micro electro-mechanical system (MEMS) pressure sensors encapsulated in sealed cavities distributed in an exoskeletal boot sole;
    determining ground contact pressure information from the sensed pressures; and,
    supplying the ground contact pressure information to a robotic control system.

* * * * *